(12) United States Patent
Singh

(10) Patent No.: US 10,631,921 B2
(45) Date of Patent: *Apr. 28, 2020

(54) COAPTIVE SURGICAL SEALING TOOL

(71) Applicant: City of Hope, Duarte, CA (US)

(72) Inventor: Gagandeep Singh, Pasadena, CA (US)

(73) Assignee: City of Hope, Duarte, CA (US)

( * ) Notice: Subject to any disclaimer, the term of this patent is extended or adjusted under 35 U.S.C. 154(b) by 208 days.

This patent is subject to a terminal disclaimer.

(21) Appl. No.: 15/852,408

(22) Filed: Dec. 22, 2017

(65) Prior Publication Data

US 2018/0185086 A1    Jul. 5, 2018

Related U.S. Application Data

(63) Continuation of application No. 15/331,228, filed on Oct. 21, 2016, now Pat. No. 9,848,942, which is a continuation of application No. 14/942,817, filed on Nov. 16, 2015, now Pat. No. 9,492,222, which is a continuation of application No. 13/842,510, filed on Mar. 15, 2013, now Pat. No. 9,186,214.

(60) Provisional application No. 61/706,603, filed on Sep. 27, 2012.

(51) Int. Cl.
  *A61B 18/14* (2006.01)
  *A61B 18/18* (2006.01)
  *A61B 18/00* (2006.01)

(52) U.S. Cl.
  CPC ...... *A61B 18/1445* (2013.01); *A61B 18/1442* (2013.01); *A61B 18/18* (2013.01); *A61B 2018/0063* (2013.01); *A61B 2018/00345* (2013.01); *A61B 2018/00404* (2013.01); *A61B 2018/00529* (2013.01)

(58) Field of Classification Search
  CPC . A61B 18/1445; A61B 18/1442; A61B 18/18; A61B 2018/0345; A61B 2018/00404; A61B 2018/00529; A61B 2018/00595; A61B 2018/0063
  See application file for complete search history.

(56) References Cited

U.S. PATENT DOCUMENTS

| | | |
|---|---|---|
| 640,517 A | 1/1900 | Acheson |
| 3,398,746 A | 8/1968 | Abramson |
| 3,732,719 A | 5/1973 | Pallotta |
| 4,241,861 A | 12/1980 | Fleischer |
| 4,671,274 A | 6/1987 | Sorochenko |
| 4,893,530 A | 1/1990 | Warheit |
| 4,938,214 A | 7/1990 | Specht et al. |
| 4,982,500 A | 1/1991 | Ramani |

(Continued)

OTHER PUBLICATIONS

Aesculap, Inc. (A B. Braun Company), Catalog—"Instruments and Devices for Bipolar Surgery," Sep. 2012. 35 pages.

(Continued)

*Primary Examiner* — Paula J Stice
(74) *Attorney, Agent, or Firm* — Mintz Levin Cohn Ferris Glovsky and Popeo, P.C.

(57) ABSTRACT

A coaptive surgical sealing tool may be similar to an ordinary hemostat with long (50, 60, 70 or 80 mm) thin jaws for sliding into the liver parenchyma, without tearing the larger blood vessels. The jaws are spring loaded and are designed for uniform compression, and to avoid closing too quickly. The jaws are capable of sealing a 50, 60, 70 or 80 mm sealing length, in a single bite, although it can also seal shorter lengths as well. The tool can be used with existing RF/bi-polar cautery generators.

13 Claims, 1 Drawing Sheet

(56) References Cited

U.S. PATENT DOCUMENTS

| | | | |
|---|---|---|---|
| 5,116,332 | A | 5/1992 | Lottick |
| 5,300,087 | A | 4/1994 | Knoepfler |
| 5,395,312 | A | 3/1995 | Desai |
| 6,010,516 | A | 1/2000 | Hulka |
| 6,679,881 | B1 | 1/2004 | Bybee |
| 6,863,669 | B2 | 3/2005 | Spitzer |
| 7,422,591 | B2 | 9/2008 | Phan |
| 9,173,707 | B2 | 11/2015 | Singh |
| 9,186,214 | B2 | 11/2015 | Singh |
| 9,186,215 | B2 | 11/2015 | Singh |
| 9,480,526 | B2 | 11/2016 | Singh |
| 9,629,676 | B2 | 4/2017 | Singh |
| 9,872,730 | B2 | 1/2018 | Singh |
| 2002/0016591 | A1 | 2/2002 | Levine et al. |
| 2003/0018331 | A1 | 1/2003 | Dycus et al. |
| 2003/0181910 | A1 | 9/2003 | Dycus et al. |
| 2005/0159745 | A1 | 7/2005 | Truckai et al. |
| 2005/0203499 | A1 | 9/2005 | Pendekanti et al. |
| 2006/0235379 | A1 | 10/2006 | McClurken et al. |
| 2007/0049920 | A1 | 3/2007 | McClurken et al. |
| 2009/0163905 | A1 | 6/2009 | Winkler et al. |
| 2011/0004208 | A1 | 1/2011 | Truckai et al. |
| 2012/0111157 | A1 | 5/2012 | Qiu |
| 2013/0018411 | A1 | 1/2013 | Collings et al. |
| 2013/0296843 | A1 | 11/2013 | Boudreaux et al. |
| 2014/0088582 | A1 | 3/2014 | Singh |
| 2014/0298661 | A1 | 10/2014 | Carmichael et al. |
| 2017/0224348 | A1 | 8/2017 | Wong et al. |
| 2018/0206917 | A1 | 7/2018 | Singh |

OTHER PUBLICATIONS

Aragon Surgical, Inc., "CAIMAN breeds confidence", Lektrafuse CAIMAN product brochure, 3 pages (Jan. 2010).

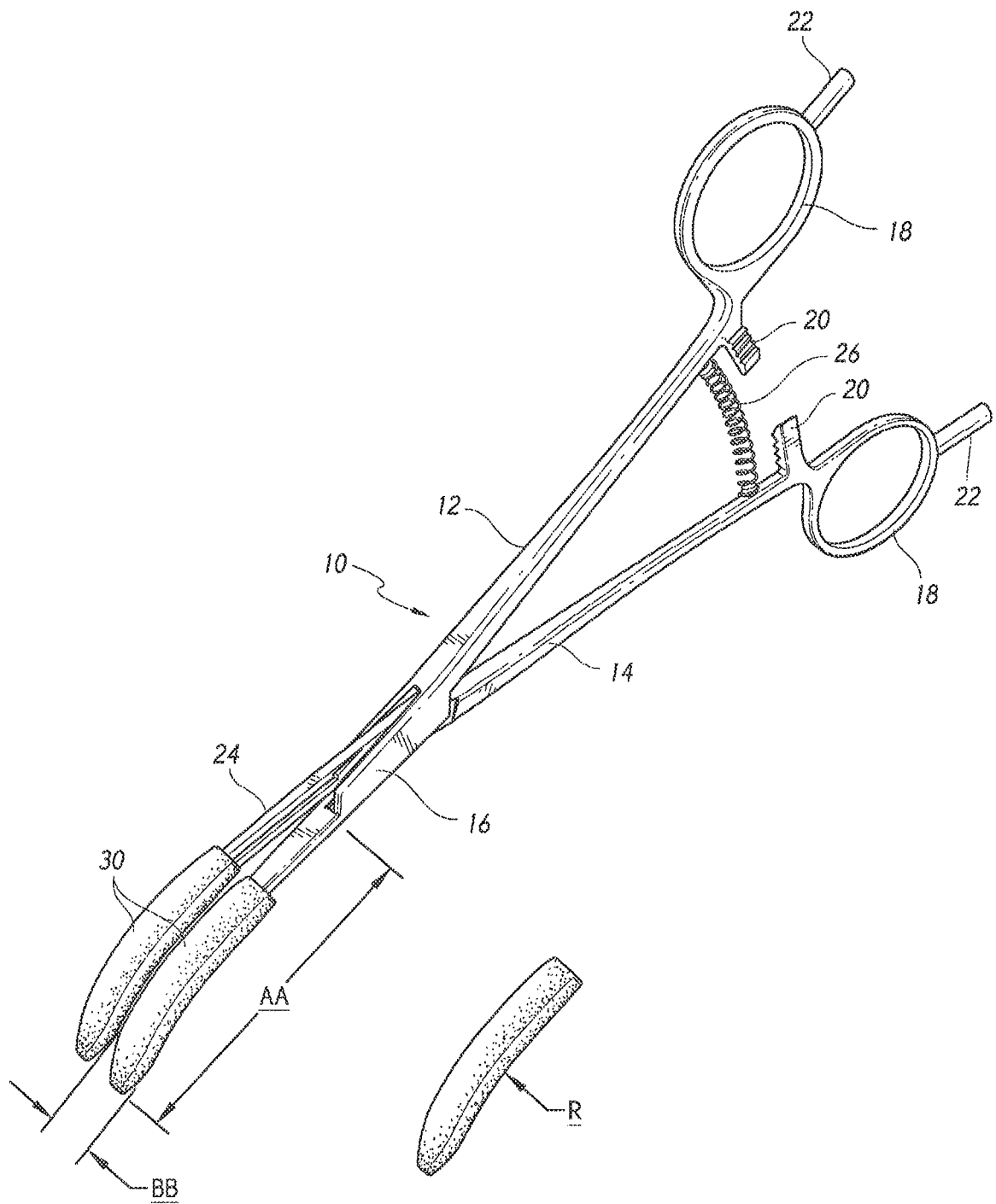

COAPTIVE SURGICAL SEALING TOOL

CROSS-REFERENCE TO RELATED APPLICATIONS

This application is a Continuation of U.S. patent application Ser. No. 15/331,228 filed on Oct. 21, 2016, entitled "Coaptive Surgical Sealing Tool", which is a Continuation of U.S. patent application Ser. No. 14/942,817 filed on Nov. 16, 2015, entitled "Coaptive Surgical Sealing Tool", now U.S. Pat. No. 9,492,222, which is a Continuation of U.S. patent application Ser. No. 13/842,510 filed Mar. 15, 2013, now U.S. Pat. No. 9,186,214, issued on Nov. 17, 2015, entitled "Coaptive Surgical Sealing Tool", which claims the benefit of U.S. Provisional Patent Application No. 61/706,603 filed Sep. 27, 2012, entitled "Coaptive Surgical Sealing Tool", of which the contents are incorporated herein by reference in their entirety.

BACKGROUND OF THE INVENTION

Removal of part of the liver (hepatic resection) is often performed to remove a tumor. Blood loss is a serious complication associated with this procedure. Multiple surgical techniques and devices have been developed to minimize blood loss and improve outcomes in hepatic resection. Several studies including a 2009 Cochrane Systematic Review of techniques for liver parenchymal transection have examined the efficacy of different methods of liver resection. Based on this review, the clamp-crush technique was favored due to low cost and with newer techniques such as cavitron ultrasound surgical aspirator (CDSA), hydrojet, and radio frequency dissecting sealer (RFDS) showing no improvement in morbidity or blood transfusion in comparison to the clamp-crush technique.

The clamp-crush technique generally involves crushing the liver parenchyma using a hemostatic clamp tool to expose small vessels and biliary radicals, which are then divided and sealed via radio frequency (RF) energy provided to the jaws of the tool. Various tools have been proposed for this purpose. However, challenges remain in providing a coaptive surgical sealing tool offering superior performance and efficiency in a simple and low-cost design. It is an object of the invention to provide an improved coaptive surgical sealing tool.

DETAILED DESCRIPTION

A coaptive surgical sealing tool may be similar to an ordinary hemostat with long (50, 60, 70 or 80 mm) thin jaws for sliding into the liver parenchyma, without tearing the larger blood vessels. The jaws are spring loaded and are designed for uniform compression, and to avoid closing too quickly. The jaws are capable of sealing a 50, 60, 70 or 80 mm sealing length, in a single bite, although it can also seal shorter lengths as well. The tool can be used with existing RF/bi-polar cautery generators, including generators the Triad-Covidean Ligasure Generator, the ConMed generator or the Enseal generator. The tool is suitable for open surgery uses, and may also be adapted for laparoscopic surgery. The tool may be provided in different sizes for different caliber of vessels. In view of its simple design, the tool may be supplied at low cost, as either a reusable or single use unit.

In use, the jaws may be closed with a gradual compression process, with a compression spring acting against the closing movement, to prevent tearing of larger blood vessels. The jaws may a slot and/or ridge, to leave a pre-grooved line for transection after the seal has been completed. The tool may reduce parenchymal transection times in excess of 50%. With 50 mm of sealing length is can seal more tissue in one bite than any existing device yet is versatile enough to seal small lengths of tissue.

DESCRIPTION OF THE DRAWING

As shown in FIG. 1, and example of the tool 10 has first and second arms 12 and 14 pivotally connected via a hinge 16. A ringer ring 18 is provided on the back or proximal end of each arm 12, 14. Each arm 12, 14 has a jaw 24 in front or distal of the hinge 16. A spring 26 urges the jaws into an open position. A lock tab 20 may be provided adjacent to each finger ring 18, to allow the jaws 24 to remain clamped or closed, against the force of the spring. The tool 10 according is similar to a hemostat clamp, and consequently benefits from ergonomic design elements of a hemostat clamp. Hence the tool 10 provides ease of use when used in open surgery. Connectors 22 may connect electrodes 30 on the jaws 24 to an RF generator.

The jaws 24 are very thin and easy to slide through the liver parenchyma without disrupting the parenchyma architecture. For example, the jaws may a length AA or 50, 60, 70 or 80 mm, and a width BB of 4, 5, 6 or 7 mm. The spring 26 helps to prevent accidentally closing down on the parenchyma to quickly which prevents parenchymal disruption. The jaws 24 may be straight or curved with a radius R of about 3-10 cm. Typically, the curvature of the jaws, if any, is in the downward direction, i.e., about an axis parallel to the axis of the hinge 16.

The electrodes 30 may extend over the full length of each jaw 24, or only partially over each jaw 24, as shown in FIG. 1. The electrodes 30 may optionally be removable and separately replaceable.

A low cost embodiment of the tool may be provided by modifying a conventional hemostat clamp having long slender jaws, to include the spring 26, the electrodes 30 and connectors 22.

Method of Use

As used for hepatic resection, the surgeon slides the jaws 24 through the liver parenchyma. With the jaws appropriately positioned around a vessel or biliary radical, the jaws 24 are slowly closed via the surgeon squeezing the finger rings 18 towards each other. The electrodes 30 on the inside of the jaws are clamped or pressed onto opposite sides of the vessel. The spring 26 acts against this closing movement, helping to provide a slow and controlled movement. With the tool 10 held momentarily in a fixed position, RF energy is then provided to the electrodes 30, sealing the vessel.

The tool may of course also be used for other surgical procedures on other organs apart from the liver.

Results

From 2010-2012, a total of 51 patients underwent >30% liver resection for malignant disease. All patients underwent open laparotomy for hepatic resection. The patient sample was diverse. The majority of patients underwent resection for metastatic disease to the liver; 4 gallbladder cancer with radical liver resection; 1 hepatocellular carcinoma; 3 patients had documented cirrhosis. Procedures included: 7 patients were combined colorectal primary and liver resection; 2 patients underwent second resection for recurrence; 7 patients had additional nanoknife procedures at the time of resection. Post-op adverse events within 30 days of surgery included 0 bile leaks; 1 blood transfusion; 1 return to operating room for colon anastomatic leak; no intra-abdominal abscess.

CONCLUSIONS

Use of the present tool as described appears to be a safe and effective technique for major hepatic resection with minimal post-operative adverse events.

The invention claimed is:

1. A surgical tool comprising:
   a first arm having a first jaw;
   a second arm having a second jaw, the first arm and second arm being movably attached to each other at a connection between the first and second arms;
   first and second removable electrodes on the first and second jaws, respectively, wherein the first and second removable electrodes extend around a circumference of at least end portions of the first and second jaws, respectively.
2. The surgical tool of claim 1 with the first and second jaws each having a width of 3-7 mm.
3. The surgical tool of claim 1 with the first and second jaws each having a width of 4-6 mm.
4. The surgical tool of claim 1 further comprising first and second connectors electrically connected to the first and second removable electrodes and adapted to connect to an RF generator.
5. The surgical tool of claim 4, further comprising at least one of a slot and ridge on at least one of the first and second jaws for leaving a pre-grooved line for transection after a vessel is sealed by the surgical tool.
6. The surgical tool of claim 5, wherein the at least one of a slot and ridge are on at least one of the first and second removable electrodes.
7. The surgical tool of claim 1, further comprising a finger ring on the back section of each arm; and a spring between the back sections of the arms, with the spring urging the back sections of the arms away from each other.
8. The surgical tool of claim 1, wherein the first and second jaws have a length of 5 to 8 cm.
9. The surgical tool of claim 1, wherein the first and second jaws are straight.
10. The surgical tool of claim 1, wherein the first and second jaws are curved and have a radius of about 3 cm to 10 cm.
11. The surgical tool of claim 1, wherein the connection is a pivot connection.
12. The surgical tool of claim 11, wherein the first and second jaws are curved about an axis parallel to an axis of the pivot connection.
13. The surgical tool of claim 1, wherein the first and second removably electrodes extend over a full length of the first and second jaws, respectively.

* * * * *